(12) United States Patent
Sampson

(10) Patent No.: US 8,481,530 B2
(45) Date of Patent: Jul. 9, 2013

(54) 3β-HYDROXYSTEROID DEHYDROGENASE INHIBITORS

(75) Inventor: Nicole Sampson, Setauket, NY (US)

(73) Assignee: The Research Foundation of State University of New York, Albany, NY (US)

( * ) Notice: Subject to any disclaimer, the term of this patent is extended or adjusted under 35 U.S.C. 154(b) by 207 days.

(21) Appl. No.: 12/517,084

(22) PCT Filed: Dec. 3, 2007

(86) PCT No.: PCT/US2007/024768
§ 371 (c)(1),
(2), (4) Date: Jan. 11, 2010

(87) PCT Pub. No.: WO2008/070039
PCT Pub. Date: Jun. 12, 2008

(65) Prior Publication Data
US 2011/0124639 A1      May 26, 2011

(51) Int. Cl.
*A61K 31/535* (2006.01)

(52) U.S. Cl.
USPC ............... 514/232.8; 514/284; 435/7.8

(58) Field of Classification Search
USPC .................. 514/232.8, 284; 435/7.8
See application file for complete search history.

(56) References Cited

U.S. PATENT DOCUMENTS 5,708,001 A    1/1998  Andrews et al.

OTHER PUBLICATIONS

Gebo, Sex Transm Infect 2002;78:147-148.*
Thomas et al, Biorganic & Medicinal Chemistry Letters 21 (2011) 2216-2219.*
International Preliminary Report on Patentability.
Frye, "Discovery and Clinical Development of Dutasteride, a Potent Dual 5α-Reductase Inhibitor," Current Topics in Medicinal Chemistry, 2006, pp. 405-421.

* cited by examiner

*Primary Examiner* — Brandon Fetterolf
*Assistant Examiner* — Jean Cornet
(74) *Attorney, Agent, or Firm* — Hoffmann & Baron, LLP

(57) ABSTRACT

The present invention relates to methods of treating a patient infected by *Actinomycetes* sp. by administering 6-aza-17-substituted-androst-4-en-3-one compounds to that patient. Another aspect of the invention relates to the screening for drug candidates to treat patients infected by *Actinomycetes* sp.

21 Claims, No Drawings

3β-HYDROXYSTEROID DEHYDROGENASE INHIBITORS

This invention was supported by a grant from NIH-NIAID, grant number R21AI065251. The United States government has rights in this invention.

This application is based on, and applicant claims priority from U.S. Provisional Application No. 60/868,219 filed Dec. 1, 2006, and PCT/US2007/24768 filed Dec. 3, 2007, which are incorporated herein by reference.

BACKGROUND OF THE INVENTION

Tuberculosis is an opportunistic infection in individuals with HIV-AIDS that is estimated to infect 30% of the world's population. There are 8.8 million new cases every year and 10% of *Mycobacterium tuberculosis* infected individuals will develop active infections. The World Health Organization estimates that two million people die every year from tuberculosis.

*Mycobacterium tuberculosis* (Mtb), the causative agent of tuberculosis, is a gram-positive *bacillus* that is a nocardioform actinomycete. Because Mtb is slow growing and evades the host immune system, the human host becomes a reservoir of the mycobacteria. Each individual with an active Mtb infection infects on average 10 to 15 more individuals. Of these infected individuals, 3-4% will develop active disease immediately, and 5-10% will develop active tuberculosis within their lifetime.

HIV infection predisposes individuals to active infection with Mtb. It is estimated that 10% of HIV positive individuals are also Mtb infected. HIV-positive individuals are much more susceptible to developing active disease and approximately 13% of AIDS deaths worldwide are due to Mtb.

Current treatment regimens require the use of multiple antibiotics over a two month period utilizing isoniazid, rifampicin, pyrazinamide and ethambutol or streptomycin, followed by another four months of treatment with isoniazid and rifampicin. The difficulty in complying with this regimen has led to bacterial resistance to front-line TB drugs rifampicin and isoniazid. Drug resistance is leading to an increased TB burden in the population.

Accordingly, new approaches are required to combat the emergence of virulent multi-drug resistant organism (MDR-TB), which are defined as simultaneously resistant to both isoniazid and rifampicin, and extensive drug-resistant organism (XDR-TB), which are defined as MDR-TB that have simultaneous resistance to three or more of the six major classes of second-line drugs. The major classes of second line drugs include aminoglycosides, polypeptides, fluoroquinolones, thioamides, cycloserine, and para-aminosalicylic acid. These new approaches to treating an AIDS-related opportunistic infection should be effective against both sensitive and drug-resistant strains of *M. tuberculosis*.

Additionally, the incidence of non-tuberculosis mycobacterium infections is increasing at an alarming rate among people with HIV-AIDS. New approaches are needed to treat these infections and diseases caused by mycobacterium.

Approaches to treating mycobacterium may also be used to target other infectious *Actinomycetes*. For instance, *Nocardia* sp. have genomes similar to that of *Mycobacterium* sp and may benefit from approaches used to treat mycobacterium.

Substituted 6-azaandrostenones were developed by scientists at Glaxo Smith Kline for use as 5α-testosterone reductase inhibitors. These compounds were described and patented in U.S. Pat. No. 5,708,001 to Andrews, et al.

SUMMARY OF THE INVENTION

The invention relates to a method for treating a patient infected by *Actinomycetes* sp., the method comprising administering to the patient an effective amount of a 6-aza-17-substituted-androst-4-en-3-one having formula (I):

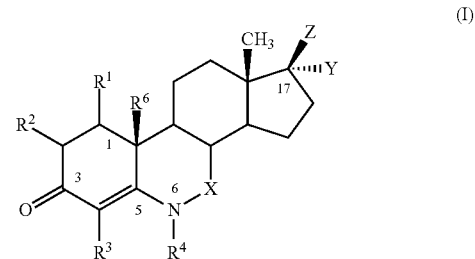

(I)

wherein
$R^1$ and $R^2$
i) are independently hydrogen or lower alkyl and the bond between the carbons bearing $R^1$ and $R^2$ is a single or a double bond, or
ii) taken together are a —$CH_2$— group forming a cyclopropane ring, and the bond between the carbons bearing $R^1$ and $R^2$ is a single bond;
$R^3$ is hydrogen, -$Alk^1$-H (optionally substituted with one or more halogens), lower cycloalkyl, lower cycloalkyl-lower alkyl), halogen, -$(Alk^1)_n$-$CO_2H$, -$(Alk^1)_n$-$CO_2R^7$, -$(Alk^1)_n$-$Ar^1$, -$(Alk^1)_n$-$CONR^8R^9$, -$(Alk^1)_n$-$NR^8R^9$, -$(Alk^1)_n$-$S(O)_r$-$R^7$, -$(Alk^1)_n$-CN, -$(Alk^1)$-OH, -$(Alk^1)$-$COR^7$ or -$(Alk^1)$-$OR^7$; wherein
$Alk^1$ is lower alkylene, lower alkenylene or lower alkynylene,
n is 0 or 1,
r is 0, 1 or 2,
$R^7$ is -$Alk^1$-H, -$(Alk^1)_n$-$Ar^1$ or lower cycloalkyl,
$R^8$ and $R^9$ are independently hydrogen, -$Alk^1$-H or lower cycloalkyl,
$Ar^1$ is a homocyclic aryl group of 6 to 14 carbons;
$R^4$ is hydrogen, -$Alk^1$-H, lower cycloalkyl, lower cycloalkyl-lower alkyl, -$(Alk^1)_n$-$S(O)_rR^7$, -$(Alk^1)_n$-phthalimidyl, -$(Alk^1)$-$CO_2H$, -$(Alk^1)_n$$CO_2R^7$, -$(Alk^1)_n$-$COR^7$, -$(Alk^1)_n$-$Ar^1$, -$(Alk^1)_n$-$CONR^8R^9$, -$(Alk^1)_n$-$NR^8R^9$, -$(Alk^1)$-OH or -$(Alk^1)$-$OR^7$;
X is,

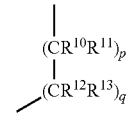

wherein $R^{10}$, $R^{11}$, $R^{12}$ and $R^{13}$ are independently hydrogen or lower alkyl, p and q are independently either 0 or 1; and,
i) Y is hydrogen or hydroxy and
Z is -$(Alk^2)_n$-$COR^5$, -$(Alk^2)_n$-$CO_2R^5$, -$(Alk^2)_n$-$COSR^5$, -$(Alk^2)_n$-$CONR^{14}R^{15}$, -$(Alk^2)$-$OCO_2R^5$, -$(Alk^2)$-$OCOR^5$—, -$(Alk^2)$-$OCONR^{14}R^{15}$, -$(Alk^2)$-$OR^5$, -$(Alk^2)$-$NR^5COR^5$, -$(Alk^2)$-$NR^5CO_2R^5$, -$(Alk^2)$-$NR^5CONR^{14}R^{15}$, -$(Alk^2)_n$-$CONR^5NR^{14}R^{15}$, -(Alk²)ₙ-CONR⁵CONR¹⁴R¹⁵, -(Alk²)-NR⁵ CSNR¹⁴ R¹⁵ or -(Alk²)ₙ-CONR⁵CSNR¹⁴R¹⁵; wherein Alk² is (C₁₋₁₂)alkylene, (C₂₋₁₂)alkenylene or (C₂₋₁₂)alkynylene, R⁵ and R⁵' are independently hydrogen, -Alk¹-H (optionally substituted independently with one or more CO₂H, CO₂R⁷, Ar², Ar³, or cyano groups), (Alk¹)ₙ-(lower cycloalkyl (optionally substituted independently with one or more -Alk¹-H groups)), adamantyl, norbornyl, Ar², Ar³, (lower cycloalkyl)-Ar² or (lower cycloalkyl)-Ar³; wherein Ar² is a homocyclic aromatic group of 6 to 14 carbon ring atoms (optionally substituted independently with one or more -Alk²-H (optionally substituted independently with one or more halogens), -(Alk¹)ₙ-COR⁷, -(Alk¹)ₙ-OH, -(Alk¹)ₙ-OR¹⁶, -(Alk¹)ₙ-Ar³, -(Alk¹)ₙ-CO₂H, -(Alk¹)ₙ-CO₂R⁷, S(O)ᵣR⁷, NR⁸S(O)ᵣR¹⁶, NR⁸R⁹, CONR⁸R⁹, lower cycloalkyl, lower alkoxy, -(Alk¹)ₙ-Ar¹ (optionally substituted with one or more -Alk¹-H or halogen), methylenedioxy, ethylenedioxy, morpholino, thiomorpholino, cyano, nitro or halogens); wherein R¹⁶ is -Alk¹-H (optionally substituted independently with one or more halogens), lower cycloalkyl (optionally substituted independently with one or more halogens, or -Alk¹-H (optionally substituted independently with one or more halogens)) or -(Alk¹)ₙ-Ar¹ (wherein Ar¹ is optionally substituted independently with one or more lower alkoxy, cyano, halogen or -Alk¹-H (optionally substituted independently with one or more halogens);

Ar³ is an aromatic group of 5 to 14 ring atoms, at least one of which is O, N or S (optionally substituted independently with one or more -Alk¹-H (optionally substituted independently with one or more halogens), lower cycloalkyl, lower alkoxy, CO₂H, CO₂R⁷, -(Alk¹)ₙ-Ar¹, cyano or halogen);

R¹⁴ and R¹⁵ are
a) independently, hydroxy, hydrogen, -Alk²-H, lower alkoxy, -(Alk¹)ₙ-adamantyl, -(Alk¹)ₙ-myrantyl, -(Alk¹)ₙ-norbornyl, -(Alk¹)ₙ-fluorenyl, -(Alk¹)ₙ-fluorenonyl, -(Alk¹)ₙ-indanyl (optionally substituted with one or more -Alk¹-H), -Alk¹-H (optionally substituted independently with one or more halogens, cyano, cycloalkyl, SR⁵, COR⁵, CONR⁵R⁷, NR⁵'COR⁵, NR⁵'CO₂R⁵, NR⁵'CONHR⁵, CO₂R⁵, OR⁵, Ar² or Ar³), Ar² or Ar³ or a saturated C₄₋₁₈ bicyclic ring or C₃₋₁₁ saturated ring, optionally containing an oxygen or sulfur atom (said rings optionally substituted independently with one or more cyano, R¹⁶, Ar² or Ar³);
b) alkylene groups (optionally substituted with one or more R⁷ groups, taken together with the linking nitrogen to form a 4 to 8 atom heterocyclic group)

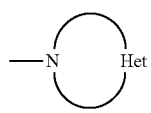

wherein;

Het represents —O—, —CH₂—, —S(O)ᵣ—, —(NH)— or —(N(Alk¹-H))—;

with the proviso that
when Z is -(Alk²)ₙ-COR⁵, -(Alk²)ₙ-CO₂R⁵ or -(Alk²)ₙ-CO-thiopyridyl and R⁵ is hydrogen, -Alk¹-H, lower cycloalkyl, or adamantyl or when Z is -(Alk²)ₙ-CONR¹⁴R¹⁵ and R¹⁴ and R¹⁵ are a) independently hydrogen, -Alk²-H, lower cycloalkyl, lower alkoxy, adamantyl, -Ar¹, benzyl, diphenylmethyl, triphenylmethyl or (Alk¹)ₙ-norbornyl; or b) carbon atoms, optionally substituted with one or more lower alkyl groups, taken together with the linking nitrogen to form a 4 to 8 atom heterocylic ring as herein before defined, Y is hydroxy;
ii) Y is hydrogen and
Z is OR⁵, OCOR⁵, OCONR¹⁴R¹⁵, NR⁵'COR⁵, NR⁵'CO₂R⁵, NR⁵CONR¹⁴R¹⁵ or NR⁵CSNR¹⁴R¹⁵; or
iii) Y and Z taken together are =O, =CH-(Alk¹)ₙ-COR⁵, =CH-(Alk¹)ₙ-CO₂ R⁵ or =CH-(Alk¹)ₙ-CONR¹⁴R¹⁵; and
R⁶ is hydrogen or methyl;
or a pharmaceutically acceptable salt or solvate thereof.

The invention also relates to a method for screening for drug candidates for treating patients infected by *Actinomycetes* sp., the method comprising:
incubating a chemical compound with a 3-beta-hydroxysteroid dehydrogenase from *Actinomycetes* sp.; and
determining whether the chemical compound binds to the 3-beta-hydroxysteroid dehydrogenase;
wherein chemical compounds that bind to the 3-beta-hydroxysteroid dehydrogenase are drug candidates.

DETAILED DESCRIPTION OF THE INVENTION

It has now been discovered that substituted 6-azaandrostenones can be used to treat infectious *Actinomycetes* sp. The substituted 6-azaandrostenones are effective against both sensitive and drug-resistant strains of infectious *Actinomycetes* sp.

Substituted 6-azaandrostenones are described in U.S. Pat. No. 5,708,001 to Andrews, et al. The generic and specific descriptions of substituted 6-azaandrostenones in the Andrews, et al. patent, the description of preparing the compounds in the Andrews, et al. patent, and the description of terms used in claim 1 from the '001 patent to Andrews, et al. is hereby incorporated by reference including, but not limited to, column 6, line 9 to column 26, line 67.

The present invention is directed to a method for treating a patient infected by *Actinomycetes* sp. The method comprises administering to the patient an effective amount of a 6-aza-17-substituted-androst-4-en-3-one compound of the Andrews, et al. patent.

The methods and compounds of the invention may be employed alone, or in combination with other anti-bacterial agents. Other anti-bacterial agents include isoniazid, rifampin, pyrazinamide, rifabutin, streptomycin and ciprofloxacin. The combination of these anti-bacterial agents and the compounds of the invention will provide new agents for the treatment of disease such as tuberculosis, including MDR-TB and XDR-TB.

An effective amount of a 6-aza-17-substituted-androst-4-en-3-one compound as used herein is any amount effective to treat a patient infected by *Actinomycetes* sp. Preferably, the 6-aza-17-substituted-androst-4-en-3-one compound is provided in an amount which has anti-bacterial activity.

In one embodiment, the compound is that of claim 1 having formula (I):

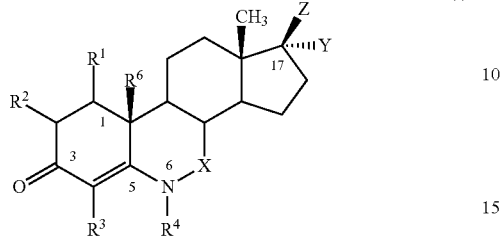

wherein
R$^1$ and R$^2$
  i) are independently hydrogen or lower alkyl and the bond between the carbons bearing R$^1$ and R$^2$ is a single or a double bond, or
  ii) taken together are a —CH$_2$— group forming a cyclopropane ring, and the bond between the carbons bearing R$^1$ and R$^2$ is a single bond;
R$^3$ is hydrogen, -Alk$^1$-H (optionally substituted with one or more halogens), lower cycloalkyl, lower cycloalkyl-lower alkyl), halogen, -(Alk$^1$)$_n$-CO$_2$H, -(Alk$^1$)$_n$-CO$_2$R$^7$, -(Alk$^1$)$_n$-Ar$^1$, -(Alk$^1$)$_n$CONR$^8$R$^9$, -(Alk$^1$)$_n$-NR$^8$R$^9$, -(Alk$^1$)$_n$-S(O)$_r$R$^7$, -(Alk$^1$)$_n$-CN, -(Alk$^1$)-OH, -(Alk$^1$)-COR$^7$ or -(Alk$^1$)-OR$^7$; wherein
  Alk$^1$ is lower alkylene, lower alkenylene or lower alkynylene,
  n is 0 or 1,
  r is 0, 1 or 2,
  R$^7$ is -Alk$^1$-H, -(Alk$^1$)$_n$-Ar$^1$ or lower cycloalkyl,
  R$^8$ and R$^9$ are independently hydrogen, -Alk$^1$-H or lower cycloalkyl,
  Ar$^1$ is a homocyclic aryl group of 6 to 14 carbons;
R$^4$ is hydrogen, -Alk$^1$-H, lower cycloalkyl, lower cycloalkyl-lower alkyl, -(Alk$^1$)$_n$-S(O)$_r$R$^7$, -(Alk$^1$)$_n$-phthalimidyl, -(Alk$^1$)-CO$_2$H, -(Alk$^1$)$_n$-CO$_2$R$^7$, -(Alk$^1$)$_n$-COR$^7$, -(Alk$^1$)$_n$-Ar$^1$, -(Alk$^1$)$_n$-CONR$^8$R$^9$, -(Alk$^1$)$_n$-NR$^8$R$^9$, -(Alk$^1$)-OH or -(Alk$^1$)-OR$^7$;
X is,

wherein R$^{10}$, R$^{11}$, R$^{12}$ and R$^{13}$ are independently hydrogen or lower alkyl, p and q are independently either 0 or 1; and,
  i) Y is hydrogen or hydroxy and
    Z is -(Alk$^2$)$_n$-COR$^5$, -(Alk$^2$)$_n$-CO$_2$R$^5$, -(Alk$^2$)$_n$-COSR$^5$, -(Alk$^2$)$_n$-CONR$^{14}$R$^{15}$, -(Alk$^2$)-OCO$_2$R$^5$, -(Alk$^2$)-OCOR$^5$-, -(Alk$^2$)-OCONR$^{14}$R$^{15}$, -(Alk$^2$)-OR$^5$, -(Alk$^2$)-NR$^{5'}$COR$^5$, -(Alk$^2$)-NR$^{5'}$CO$_2$R$^5$, -(Alk$^2$)-NR$^5$CONR$^{14}$R$^{15}$, -(Alk$^2$)$_n$-CONR$^5$NR$^{14}$R$^{15}$, -(Alk$^2$)$_n$-CONR$^5$CONR$^{14}$R$^{15}$, -(Alk$^2$)-NR$^5$CSNR$^{14}$R$^{15}$ or -(Alk$^2$)$_n$-CONR$^5$CSNR$^{14}$R$^{15}$;
    wherein
      Alk$^2$ is (C$_{1-12}$) alkylene, (C$_{2-12}$) alkenylene or (C$_{2-12}$) alkynylene, R$^5$ and R$^{5'}$ are independently hydrogen, -Alk$^1$-H (optionally substituted independently with one or more CO$_2$H, CO$_2$R$^7$, Ar$^2$, Ar$^3$, or cyano groups), (Alk$^1$)$_n$-(lower cycloalkyl (optionally substituted independently with one or more -Alk$^1$-H groups)), adamantyl, norbornyl, Ar$^2$, Ar$^3$, (lower cycloalkyl)-Ar$^2$ or (lower cycloalkyl)-Ar$^3$; wherein
  Ar$^2$ is a homocyclic aromatic group of 6 to 14 carbon ring atoms (optionally substituted independently with one or more -Alk$^2$-H (optionally substituted independently with one or more halogens), -(Alk$^1$)$_n$-COR$^7$, -(Alk$^1$)$_n$-OH, -(Alk$^1$)$_n$-OR$^{16}$, -(Alk$^1$)$_n$-Ar$^3$, -(Alk$^1$)$_n$-CO$_2$H, -(Alk$^1$)$_n$-CO$_2$R$^7$, S(O)$_r$R$^7$, NR$^8$S(O)$_r$R$^{16}$, NR$^8$R$^9$, CONR$^8$R$^9$, lower cycloalkyl, lower alkoxy, -(Alk$^1$)$_n$-Ar$^1$ (optionally substituted with one or more -Alk$^1$-H or halogen), methylenedioxy, ethylenedioxy, morpholino, thiomorpholino, cyano, nitro or halogens); wherein
    R$^{16}$ is -Alk$^1$-H (optionally substituted independently with one or more halogens), lower cycloalkyl (optionally substituted independently with one or more halogens, or -Alk$^1$-H (optionally substituted independently with one or more halogens)) or -(Alk$^1$)$_n$-Ar$^1$ (wherein Ar$^1$ is optionally substituted independently with one or more lower alkoxy, cyano, halogen or -Alk$^1$-H (optionally substituted independently with one or more halogens);
  Ar$^3$ is an aromatic group of 5 to 14 ring atoms, at least one of which is O, N or S (optionally substituted independently with one or more -Alk$^1$-H (optionally substituted independently with one or more halogens), lower cycloalkyl, lower alkoxy, CO$_2$H, CO$_2$R$^7$, -(Alk$^1$)$_n$-Ar$^1$, cyano or halogen);
R$^{14}$ and R$^{15}$ are
  a) independently, hydroxy, hydrogen, -Alk$^2$-H, lower alkoxy, -(Alk$^1$)$_n$-adamantyl, -(Alk$^1$)$_n$-myrantyl, -(Alk$^1$)$_n$-norbornyl, -(Alk$^1$)$_n$-fluorenyl, -(Alk$^1$)$_n$-fluorenonyl, -(Alk$^1$)$_n$-indanyl (optionally substituted with one or more -Alk$^1$-H), -Alk$^1$-H (optionally substituted independently with one or more halogens, cyano, cycloalkyl, SR$^5$, COR$^5$, CONR$^5$R$^7$, NR$^{5'}$COR$^5$, NR$^{5'}$CO$_2$R$^5$, NR$^{5'}$CONHR$^5$, CO$_2$R$^5$, OR$^5$, Ar$^2$ or Ar$^3$), Ar$^2$ or Ar$^3$ or a saturated C$_{4-18}$ bicyclic ring or C$_{3-11}$ saturated ring, optionally containing an oxygen or sulfur atom (said rings optionally substituted independently with one or more cyano, R$^{16}$, Ar$^2$ or Ar$^3$);
  b) alkylene groups (optionally substituted with one or more R$^7$ groups, taken together with the linking nitrogen to form a 4 to 8 atom heterocyclic group)

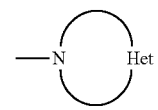

wherein;
  Het represents —O—, —CH$_2$—, —S(O)$_r$—, —(NH)— or —(N(Alk$^1$-H))—;
with the proviso that
  when Z is -(Alk$^2$)$_n$-COR$^5$, -(Alk$^2$)$_n$-CO$_2$R$^5$ or -(Alk$^2$)$_n$-CO-thiopyridyl and R$^5$ is hydrogen, -Alk$^1$-H, lower cycloalkyl, or adamantyl or when Z is -(Alk$^2$)$_n$-CONR$^{14}$R$^{15}$ and R$^{14}$ and R$^{15}$ are
  a) independently hydrogen, -Alk$^2$-H, lower cycloalkyl, lower alkoxy, adamantyl, -Ar$^1$, benzyl, diphenylmethyl, triphenylmethyl or -(Alk$^1$)$_n$ -norbornyl; or
  b) carbon atoms, optionally substituted with one or more lower alkyl groups, taken together with the linking nitrogen to form a 4 to 8 atom heterocylic ring as herein before defined,
Y is hydroxy;
ii) Y is hydrogen and
  Z is OR$^5$, OCOR$^5$, OCONR$^{14}$R$^{15}$, NR$^{5'}$COR$^5$, NR$^{5'}$CO$_2$R$^5$, NR$^5$CONR$^{14}$R$^{15}$ or NR$^5$CSNR$^{14}$R$^{15}$; or
iii) Y and Z taken together are =O, =CH-(Alk$^1$)$_n$-COR$^5$, =CH-(Alk$^1$)$_n$-CO$_2$R$^5$ or =CH-(Alk$^1$)$_n$-CONR$^{14}$R$^{15}$; and
R$^6$ is hydrogen or methyl;
or a pharmaceutically acceptable salt or solvate thereof.

In another embodiment, the compound is that of claim 2 having formula (I) wherein:
R$^1$, R$^2$, R$^3$, R$^4$, and Y are hydrogen;
R$^6$ is methyl;
X is CH$_2$;
Z represents —COR$^5$, —CO$_2$R$^5$, —COSR$^5$, or —CONR$^{14}$R$^{15}$; wherein
  R$^5$ and R$^{5'}$ are independently hydrogen, -Alk$^1$-H (optionally substituted independently with one or more CO$_2$H, CO$_2$R$^7$, Ar$^2$, Ar$^3$, or cyano groups), (Alk$^1$)$_n$-(lower cycloalkyl (optionally substituted independently with one or more -Alk$^1$-H groups)), adamantyl, norbornyl, Ar$^2$, Ar$^3$, (lower cycloalkyl)-Ar$^2$ or (lower cycloalkyl)-Ar$^3$; wherein
  Alk$^1$ is lower alkylene, lower alkenylene or lower alkynylene;
  n is 0 or 1;
  R$^7$ is -Alk$^1$-H, -(Alk$^1$)$_n$-Ar$^1$ or lower cycloalkyl;
  Ar$^2$ is a homocyclic aromatic group of 6 to 14 carbon ring atoms (optionally substituted independently with one or more -Alk$^2$-H (optionally substituted independently with one or more halogens), -(Alk$^1$)$_n$-COR$^7$, -(Alk$^1$)$_n$-OH, -(Alk$^1$)$_n$-OR$^{16}$, -(Alk$^1$)$_n$-Ar$^3$, -(Alk$^1$)$_n$-CO$_2$H, -(Alk$^1$)$_n$-CO$_2$R$^7$, S(O)$_r$R$^7$, NR$^8$S(O)$_r$R$^{16}$, NR$^8$R$^9$, CONR$^8$R$^9$, lower cycloalkyl, lower alkoxy, -(Alk$^1$)$_n$-Ar$^1$ (optionally substituted with one or more -Alk$^1$-H or halogen), methylenedioxy, ethylenedioxy, morpholino, thiomorpholino, cyano, nitro or halogens); wherein
  Alk$^2$ is (C$_{1-12}$) alkylene, (C$_{2-12}$) alkenylene or (C$_{2-12}$) alkynylene;
  r is 0, 1, or 2;
  R$^8$ and R$^9$ are independently hydrogen, -Alk$^1$-H or lower cycloalkyl;
  Ar$^1$ is a homocyclic aryl group of 6 to 14 carbons;
  R$^{16}$ is -Alk$^1$-H (optionally substituted independently with one or more halogens), lower cycloalkyl (optionally substituted independently with one or more halogens, or -Alk$^1$-H (optionally substituted independently with one or more halogens)) or -(Alk$^1$)$_n$-Ar$^1$ (wherein Ar$^1$ is optionally substituted independently with one or more lower alkoxy, cyano, halogen or -Alk$^1$-H (optionally substituted independently with one or more halogens);
  Ar$^3$ is an aromatic group of 5 to 14 ring atoms, at least one of which is O, N or S (optionally substituted independently with one or more -Alk$^1$-H (optionally substituted independently with one or more halogens), lower cycloalkyl, lower alkoxy, CO$_2$H, CO$_2$R$^7$, -(Alk$^1$)$_n$-Ar$^1$, cyano or halogen); and
R$^{14}$ and R$^{15}$ are
  a) independently, hydroxy, hydrogen, -Alk$^2$-H, lower alkoxy, -(Alk$^1$)$_n$-adamantyl, -(Alk$^1$)$_n$-myrantyl, -(Alk$^1$)$_n$-norbornyl, -(Alk$^1$)$_n$-fluorenyl, -(Alk$^1$)$_n$-fluorenonyl, -(Alk$^1$)$_n$-indanyl (optionally substituted with one or more -Alk$^1$-H), -Alk$^1$-H (optionally substituted independently with one or more halogens, cyano, cycloalkyl, SR$^5$, COR$^5$, CONR$^5$R$^7$, NR$^{5'}$COR$^5$, NR$^{5'}$CO$_2$R$^5$NR$^{5'}$CONHR$^5$, CO$_2$R$^5$, OR$^5$, Ar$^2$ or Ar$^3$), Ar$^2$ or Ar$^3$ or a saturated C$_{4-18}$ bicyclic ring or C$_{3-11}$ saturated ring, optionally containing an oxygen or sulfur atom (said rings optionally substituted independently with one or more cyano, R$^{16}$, Ar$^2$ or Ar$^3$); or
  b) alkylene groups (optionally substituted with one or more R$^7$ groups, taken together with the linking nitrogen to form a 4 to 8 atom heterocyclic group)

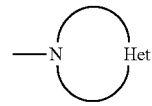

wherein;
  Het represents —O—, —CH$_2$—, —S(O)$_r$—, —(NH)— or —(N(Alk$^1$-H))—.

In yet another embodiment, the compound is that of claim 3 having formula (I) wherein:
R$^1$, R$^2$, R$^3$, R$^4$, and Y are hydrogen;
R$^6$ is methyl;
X is CH$_2$;
Z represents —COR$^5$ or —CONR$^{14}$R$^{15}$; wherein
  R$^5$ and R$^{5'}$ are independently hydrogen, -Alk$^1$-H (optionally substituted independently with one or more CO$_2$H, CO$_2$R$^7$, Ar$^2$, Ar$^3$, or cyano groups), (Alk$^1$)$_n$-(lower cycloalkyl (optionally substituted independently with one or more -Alk$^1$-H groups)), adamantyl, norbornyl, Ar$^2$, Ar$^3$, (lower cycloalkyl)-Ar$^2$ or (lower cycloalkyl)-Ar$^3$; wherein
  Alk$^1$ is lower alkylene, lower alkenylene or lower allcynylene;
  n is 0 or 1;
  R$^7$ is -Alk$^1$-H, -(Alk$^1$)$_n$-Ar$^1$ or lower cycloalkyl;
  Ar$^2$ is a homocyclic aromatic group of 6 to 14 carbon ring atoms (optionally substituted independently with one or more -Alk$^2$-H (optionally substituted independently with one or more halogens), -(Alk$^1$)$_n$-COR$^7$, -(Alk$^1$)$_n$-OH, -(Alk$^1$)$_n$-OR$^{16}$, -(Alk$^1$)$_n$-Ar$^3$, -(Alk$^1$)$_n$-CO$_2$H, -(Alk$^1$)$_n$-CO$_2$R$^7$, S(O)$_r$R$^7$, NR$^8$S(O)$_r$R$^{16}$, NR$^8$R$^9$, CONR$^8$R$^9$, lower cycloalkyl, lower alkoxy, -(Alk$^1$)$_n$-Ar$^1$ (optionally substituted with one or more -Alk$^1$-H or halogen), methylenedioxy, ethylenedioxy, morpholino, thiomorpholino, cyano, nitro or halogens); wherein
  Alk$^2$ is (C$_{1-12}$) alkylene, (C$_{2-12}$) alkenylene or (C$_{2-12}$) alkynylene;
  r is 0, 1, or 2;
  R$^8$ and R$^9$ are independently hydrogen, -Alk$^1$-H or lower cycloalkyl;
  Ar$^1$ is a homocyclic aryl group of 6 to 14 carbons;
  R$^{16}$ is -Alk$^1$-H (optionally substituted independently with one or more halogens), lower cycloalkyl (optionally substituted independently with one or more halogens, or -Alk$^1$-H (optionally substituted independently with one or more halogens)) or -(Alk$^1$)$_n$-Ar$^1$ (wherein Ar$^1$ is optionally substituted independently with one or more lower alkoxy, cyano, halogen or -Alk$^1$-H (optionally substituted independently with one or more halogens);

Ar$^3$ is an aromatic group of 5 to 14 ring atoms, at least one of which is O, N or S (optionally substituted independently with one or more -Alk$^1$-H (optionally substituted independently with one or more halogens), lower cycloalkyl, lower alkoxy, CO$_2$H, CO$_2$R$^7$, -(Alk$^1$)$_n$-Ar$^1$, cyano or halogen); and R$^{14}$ and R$^{15}$ are
a) independently, hydroxy, hydrogen, -Alk$^2$-H, lower alkoxy, -(Alk$^1$)$_n$-adamantyl, -(Alk$^1$)$_n$-myrantyl, -(Alk$^1$)$_n$-norbornyl, -(Alk$^1$)$_n$-fluorenyl, -(Alk$^1$)$_n$-fluorenonyl, -(Alk$^1$)$_n$-indanyl (optionally substituted with one or more -Alk$^1$-H), -Alk$^1$-H (optionally substituted independently with one or more halogens, cyano, cycloalkyl, SR$^5$, COR$^5$, CONR$^5$R$^7$, NR$^{5'}$COR$^5$, NR$^{5'}$CO$_2$R$^5$, NR$^{5'}$CONHR$^5$, CO$_2$R$^5$, OR$^5$, Ar$^2$ or Ar$^3$), Ar$^2$ or Ar$^3$ or a saturated C$_{4-18}$ bicyclic ring or C$_{3-11}$ saturated ring, optionally containing an oxygen or sulfur atom (said rings optionally substituted independently with one or more cyano, R$^{16}$, Ar$^2$ or Ar$^3$); or
b) alkylene groups (optionally substituted with one or more R$^7$ groups, taken together with the linking nitrogen to form a 4 to 8 atom heterocyclic group)

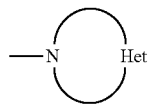

wherein;
Het represents —O—, —CH$_2$—, —S(O)$_r$—, —(NH)— or —(N(Alk$^1$-H))—.

In particular, the compounds listed in Table III of Frye, Current Topics in Medicinal Chemistry, Vol. 6, No. 5, pp. 411 (2006) are useful in the present invention. Table III of Frye is hereby incorporated by reference.

In a preferred embodiment, the compound is that of claim 3 where Z is represented by —CONR$^{14}$R$^{15}$. R$^{14}$ is hydrogen and R$^{15}$ is -(2-tert-butyl, 5-trifluoromethyl)phenyl.

In another preferred embodiment, the compound is that of claim 2 where Z is represented by —CO$_2$R$^5$. R$^5$ is hydrogen.

In yet another preferred embodiment, the compounds is that of claim 3 where Z is represented by —CONR$^{14}$R$^{15}$. R$^{14}$ is hydrogen and R$^{15}$ is -(2-benzoyl)phenyl.

Modes of administration and doses can be determined by those having skill in the art. An effective amount of the 6-aza-17-substituted-androst-4-en-3-one compound will vary with the group of patients (age, sex, weight, etc.), the nature and severity of the condition to be treated, the particular 6-aza-17-substituted-androst-4-en-3-one administered, and its route of administration. Amounts suitable for administration to humans are routinely determined by physicians and clinicians during clinical trials.

The minimum dose of the 6-aza-17-substituted-androst-4-en-3-one compound is the lowest dose at which efficacy is observed. For example, the minimum dose of the 6-aza-17-substituted-androst-4-en-3-one compound may be about 0.1 mg/kg/day, about 1 mg/kg/day, or about 3 mg/kg/day.

The maximum dose of the 6-aza-17-substituted-androst-4-en-3-one compound is the highest dose at which efficacy is observed in a patient, and side effects are tolerable. For example, the maximum dose of the 6-aza-17-substituted-androst-4-en-3-one compound may be about 10 mg/kg/day, about 9 mg/kg/day, or about 8 mg/kg/day.

The 6-aza-17-substituted-androst-4-en-3-one compounds can be administered systematically by the parenteral and enteral routes, which also include controlled release delivery systems. For example, the 6-aza-17-substituted-androst-4-en-3-one compounds of the present invention can be easily administered intravenously (e.g., intravenous injection). Intravenous administration can be accomplished by mixing the 6-aza-17-substituted-androst-4-en-3-one compounds in a suitable pharmaceutical carrier (vehicle) or excipient as understood by practitioners in the art.

Oral or enteral use is also contemplated, and formulations such as tablets, capsules, pills, troches, elixirs, suspensions, syrups, wafers, chewing gum and the like can be employed to provide the 6-aza-17-substituted-androst-4-en-3-one compounds.

Alternatively, the 6-aza-17-substituted-androst-4-en-3-one compound can be delivered by topical administration in the case of dermatological disorders such as those caused by *M. leprae* infection. The carrier should accordingly be suited for topical use. Compositions deemed suitable for such topical use include gels, salves, lotions, creams, ointments, and the like.

The 6-aza-17-substituted-androst-4-en-3-one compounds can be used to treat patients infected by *Actinomycetes* sp. Genera of actinomycetes that can be treated in accordance with the methods of the present invention include, but are not limited to, mycobacertium and nocardia. Species of mycobacterium that can be treated in accordance with the methods of the present invention include, but are not limited to, *M. abscessus, M. africanum, M. asiaticum, Mycobacterium avium* complex, *M. bovis, M. chelonae, M. fortuitum, M. gordonae, M. haemophilum, M. intracellulare, M. kansasii, M. lentiflavum, M. leprae, M. liflandii, M. malmoense, M. marinum, M. microti, M. phlei, M. pseudoshottsii, M. scrofulaceum, M. shottsii, M. smegmatis, M. triplex, M. tuberculosis, M. ulcerans, M. uvium,* and *M. xenopi.*

The methods of the present invention are useful in treating mycobacteria that cause tuberculosis and Hansen's disease. Some examples of mycobacteria that cause tuberculosis include *M. tuberculosis, M. bovis, M. africanum,* and *M. microti.* Hansen's disease, otherwise known as leprosy, is caused by *M. leprae.*

The methods of the present invention are also useful in treating nontuberculous mycobateria that cause pulmonary disease. *Mycobacterium avium-intracellulare* complex, *M. kansasii,* and *M. xenopi* are examples of such mycobacteria.

Species of nocardia that can be treated in accordance with the methods of the present invention include, but are not limited to, *N. asteroides* complex, *N. brasiliensis, N. otitidis-caviarum,* and *N. transvalensis. N. asteroides* complex, the most common pathogenic *Nocardia* sp., includes *N. asteroides*, *N. farcinica*, and *N. nova*.

The methods of the present invention are also useful in treating conditions and diseases caused by nocardia infections. Some examples of such diseases include nocardiosis, pneumonia, mycetoma, and cellulitis. *N. asteroides* complex causes nocardiosis and pneumonia.

Another aspect of the invention relates to methods for screening for drug candidates useful in treating patients infected by *Actinomycetes* sp. A drug candidate is a molecule that has the potential to be a useful medicament, pending further biological tests.

The first step in the method of screening for drug candidates is incubating a chemical compound with a 3-beta-hydroxysteroid dehydrogenase from *Actinomycetes* sp. The chemical compound can be any compound, such as those described in the '001 patent to Andrews, et al.

Incubation occurs under conditions well known to those in the art. Typically, the incubation occurs at room temperature to about 37° C. for a period of time that allows a drug candidate to bind to a 3-beta-hydroxysteroid dehydrogenase. For example, incubation may occur for one hour or for 24 hours.

The 3-beta-hydroxysteroid dehydrogenase useful in the present invention are specific to *Actinomycetes* sp. and strains of *Actinomycetes* sp. The 3-beta-hydroxysteroid dehydrogenase include, but are not limited to, the following: RV1106c in the H37Rv strain of *M. tuberculosis*, MT1137 in the CDC1551 strain of *M. tuberculosis*, ML 1942 in *M. leprae*, Mb1136c in *M. bovis*, and Q03704 in *N. farcinica*.

The next step in screening is to determine whether the chemical compound binds to the 3-beta-hydroxysteroid dehydrogenase. Binding can be determined by any method known in the art.

For example, the chemical compound or the 3-beta-hydroxysteroid dehydrogenase is immobilized to a solid support. Immobilization may be accomplished by directly binding the compound or protein to a solid surface, such as a microtiter well, a glass bead, or a resin in a column. The component that is not immobilized is usually labeled. Thus, if the chemical compound is immobilized, the protein is labeled. If the protein is immobilized, the chemical compound is labeled.

Methods for labeling proteins and chemical compounds are commonly known in the art. For instance, the label may be radioactive. Some examples of useful radioactive labels include $^{32}P$, $^{125}I$, $^{131}I$, $^{35}S$, $^{14}C$, and $^{3}H$. Use of radioactive labels have been described in U.K. 2,034,323, U.S. Pat. No. 4,358,535, and U.S. Pat. No. 4,302,204.

Some examples of non-radioactive labels include enzymes, chromophores, atoms and molecules detectable by electron microscopy, and metal detectable by their magnetic properties.

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

After contacting the chemical compound and 3-beta-hydroxysteroid dehydrogenase, detection of binding of the chemical compound and 3-beta-hydroxysteroid dehydrogenase, for example by detecting a label, indicates that the chemical compound is a drug candidate.

The method of screening for drug candidates optionally comprises the further step of determining whether the chemical compound inhibits the 3-beta-hydroxysteroid dehydrogenase from *Actinomycetes* sp. Any method known to those skilled in the art can be employed to determine whether the drug candidate inhibits the 3-beta-hydroxysteroid dehydrogenase from *Actinomycetes* sp.

For example, an in vitro culture of *E. coli* or *Strepomyces* transformed cells can be incubated with the drug candidate. The culture can them be assayed, by any method known to those in the art, to determine whether the drug candidate inhibited proliferation compared to a control culture without the drug candidate. See Example 1 below.

Alternatively, in vivo assays can be employed. Such assays are well known to those skilled in the art. For instance, laboratory animals, such as mice and rats, can be infected with *Actinomycetes* sp. and then administered a drug candidate or control compound at specific dosages for a specified period of time. The mammals are sacrificed at selected time points. The number of bacterial cfu is determined.

EXAMPLES

The 6-aza-17-substituted-androst-4-en-3-one compounds useful in the methods of the present invention can be made by methods known in the art. Examples of suitable methods for preparing the 6-aza-17-substituted-androst-4-en-3-one compounds useful in the methods of the present invention are described in the Andrews, et al. patent, U.S. Pat. No. 5,708, 001 The specific examples found in the Andrews, et al. patent are incorporated herein by reference.

Examples have been set forth below for the purpose of illustration and to describe the best mode of the invention at the present time. The scope of the invention is not to be in any way limited by the examples set forth herein.

Example 1

In Vitro Assay

Enzyme activities may be determined from *E. coli* or *Strepomyces* transformed cells that heterologously express mycobacterial or nocardial 3β-hydroxysteroid dehydrogenase or native mycobacterial cells that have been grown in the presence of cholesterol. Purified protein is prepared by homogenization of the cells, centrifugation, fractionation with 5-10% (w/v) ammonium sulfate, anion exchange chromatography with DEAE-cellulose followed by Q-Sepharose, and gel filtration with a Sephacryl S-200 high-resolution column. Pure fractions containing dehydrogenase activity are collected and concentrated.

The purified enzyme may be assayed with 150 µM dehydroepiandrosterone and 3.5 mM NAD+ and varying amounts of the test compound, i.e., a compound of formula I, in buffer. Corresponding incubations are carried out with no test compound as a control experiment. Assay components except dehydrogenase are preincubated for 10 minutes at pH 8.5, and following the addition of dehydrogenase are allowed to proceed for 10-30 minutes. The initial velocity of product formation is measured using ultraviolet/visible spectroscopy (UV/vis) with detection of the product NADH at 340 nm and compared to the corresponding velocity in the control experiment. The results of these assays appear as $IC_{50}$'s reported in Table 1.

TABLE 1

3β-hydroxysteroid dehydrogenase In Vitro Inhibitory Activity

| Compound | IC$_{50}$ *M. tuberculosis* 3β-hydroxysteroid dehydrogenase |
|---|---|
| (steroid with carboxylic acid) | + |
| (steroid amide with 2-tert-butyl-5-trifluoromethylphenyl) | ++ |
| (steroid amide with 2-benzoylphenyl) | ++ |
| (steroid amide with 2,5-di-tert-butylphenyl) | ++ |
| (steroid amide with 4-morpholinophenyl) | + |

TABLE 1-continued

3β-hydroxysteroid dehydrogenase In Vitro Inhibitory Activity

| Compound | $IC_{50}$ M. tuberculosis 3β-hydroxysteroid dehydrogenase |
|---|---|
| (steroid structure) | +++ |
| (steroid structure) | ++ |

+ = >50 μM
++ = 1-50 μM
+++ = <1 μM

Example 2

In Vivo Assay

Laboratory animals, such as mice, guinea pigs, or rabbits, are infected with mycobacteria by nebulizer, intratracheally, or intravenously to deliver infectious agent to the mouse. Varying amounts of the test compound, i.e. a compound of formula I, formulated as known to those in the art are administered to the animals over a period of time. Corresponding infections are carried out with no test compound as a control experiment. The animals are sacrificed at selected time points and the number of bacterial cfu are determined by homogenizing a lung in PBS containing 0.05% Tween 80, plating lung homogenates on Middlebrook 7H10 agar (Difco) containing 10% OADC (Difco) and 0.5% glycerol, and incubating at 37° C. for 3-4 weeks before counting colonies to determine cfu.

I claim:

1. A method for treating a patient infected by *Actinomycetes* sp., the method comprising administering to the patient an effective amount of a 6-aza-17-substituted-androst-4-en-3-one having formula (I):

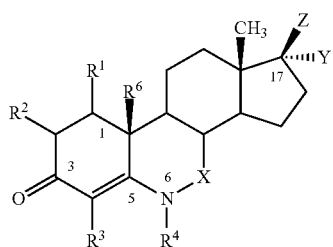

wherein
$R^1$ and $R^2$
  i) are independently hydrogen or lower alkyl and the bond between the carbons bearing $R^1$ and $R^2$ is a single or a double bond, or
  ii) taken together are a —$CH_2$— group forming a cyclopropane ring, and the bond between the carbons bearing $R^1$ and $R^2$ is a single bond;
$R^3$ is hydrogen, -$Alk^1$-H (optionally substituted with one or more halogens), lower cycloalkyl, lower cycloalkyl-lower alkyl, halogen, -$(Alk^1)_n$-$CO_2H$, -$(Alk^1)_n$-$CO_2R^7$, -$(Alk^1)_n$-$Ar^1$, -$(Alk^1)_n$-$CONR^8R^9$, -$(Alk^1)_n$-$NR^8R^9$, -$(Alk^1)_n$-$S(O)_rR^7$, -$(Alk^1)_n$-CN, -$(Alk^1)$-OH, -$(Alk^1)$-$COR^7$ or -$(Alk^1)$-$OR^7$; wherein Alk¹ is lower alkylene, lower alkenylene or lower alkynylene,
n is 0 or 1,
r is 0, 1 or 2,
$R^7$ is -Alk¹-H, -(Alk¹)$_n$-Ar¹ or lower cycloalkyl,
$R^8$ and $R^9$ are independently hydrogen, -Alk¹-H or lower cycloalkyl,
Ar¹ is a homocyclic aryl group of 6 to 14 carbons;
$R^4$ is hydrogen, -Alk¹-H, lower cycloalkyl, lower cycloalkyl-lower alkyl, -(Alk¹)$_n$-S(O)$_r$R⁷, -(Alk¹)$_n$-phthalimidyl, -(Alk¹)-CO₂H, -(Alk¹)$_n$-CO₂R⁷, -(Alk¹)$_n$-COR⁷, -(Alk¹)$_n$-Ar¹, -(Alk¹)$_n$-CONR⁸R⁹, -(Alk¹)$_n$-NR⁸R⁹, -(Alk¹)-OH or -(Alk¹)-OR⁷;
X is,

wherein $R^{10}$, $R^{11}$, $R^{12}$ and $R^{13}$ are independently hydrogen or lower alkyl, p and q are independently either 0 or 1; and,
i) Y is hydrogen or hydroxy and
Z is -(Alk²)$_n$-COR⁵, -(Alk²)$_n$-CO₂R⁵, -(Alk²)$_n$-COSR⁵, -(Alk²)$_n$-CONR¹⁴R¹⁵, -(Alk²)-OCO₂R⁵, -(Alk²)-OCOR⁵—, -(Alk²)-OCONR¹⁴R¹⁵, -(Alk²)-OR⁵, -(Alk²)-NR⁵'COR⁵, -(Alk²)-NR⁵'CO₂R⁵, -(Alk²)-NR⁵CONR¹⁴R¹⁵, -(Alk²)$_n$-CONR⁵NR¹⁴R¹⁵, -(Alk²)$_n$-CONR⁵CONR¹⁴R¹⁵, -(Alk²)-NR⁵CSNR¹⁴R¹⁵ or -(Alk²)$_n$-CONR⁵CSNR¹⁴R¹⁵; wherein
Alk² is (C₁₋₁₂) alkylene, (C₂₋₁₂) alkenylene or (C₂₋₁₂) alkynylene,
$R^5$ and $R^{5'}$ are independently hydrogen, -Alk¹-H (optionally substituted independently with one or more CO₂H, CO₂R⁷, Ar², Ar³, or cyano groups), (Alk¹)$_n$-(lower cycloalkyl (optionally substituted independently with one or more -Alk¹-H groups)), adamantyl, norbornyl, Ar², Ar³, (lower cycloalkyl)-Ar² or (lower cycloalkyl)-Ar³; wherein
Ar² is a homocyclic aromatic group of 6 to 14 carbon ring atoms (optionally substituted independently with one or more -Alk²-H (optionally substituted independently with one or more halogens), -(Alk¹)$_n$-COR⁷, -(Alk¹)$_n$OH, -(Alk¹)$_n$-OR¹⁶, -(Alk¹)$_n$-Ar³, -(Alk¹)$_n$-CO₂H, -(Alk¹)$_n$-CO₂R⁷, S(O)$_r$R⁷, NR⁸S(O)$_r$R¹⁶, NR⁸R⁹, CONR⁸R⁹, lower cycloalkyl, lower alkoxy, -(Alk¹)$_n$-Ar¹ (optionally substituted with one or more -Alk¹-H or halogen), methylenedioxy, ethylenedioxy, morpholino, thiomorpholino, cyano, nitro or halogens); wherein
$R^{16}$ is -Alk¹-H (optionally substituted independently with one Or more halogens), lower cycloalkyl (optionally substituted independently with one or more halogens, or -Alk¹-H (optionally substituted independently with one or more halogens)) or -(Alk¹)$_n$-Ar¹ (wherein Ar¹ is optionally substituted independently with one or more lower alkoxy, cyano, halogen or -Alk¹-H (optionally substituted independently with one or more halogens);

Ar³ is an aromatic group of 5 to 14 ring atoms, at least one of which is O, N or S (optionally substituted independently with one or more -Alk¹-H (optionally substituted independently with one or more halogens), lower cycloalkyl, lower alkoxy, CO₂H, CO₂R⁷, -(Alk¹)$_n$-Ar¹, cyano or halogen);
$R^{14}$ and $R^{15}$ are
a) independently, hydroxy, hydrogen, -Alk²-H, lower alkoxy, -(Alk¹)$_n$-adamantyl, -(Alk¹)$_n$-myrantyl, -(Alk¹)$_n$-norbornyl, -(Alk¹)$_n$-fluorenyl, -(Alk¹)$_n$-fluorenonyl, -(Alk¹)$_n$-indanyl (optionally substituted with one or more -Alk¹-H), -Alk¹-H (optionally substituted independently with one or more halogens, cyano, cycloalkyl, SR⁵, COR⁵, CONR⁵R⁷, NR⁵'COR⁵, NR⁵'CO₂R⁵, NR⁵'CONHR⁵, CO₂R⁵, OR⁵, Ar² or Ar³), Ar² or Ar³ or a saturated C₄₋₁₈ bicyclic ring or C₃₋₁₁ saturated ring, optionally containing an oxygen or sulfur atom (said rings optionally substituted independently with one or more cyano, R¹⁶, Ar² or Ar³);
b) alkylene groups (optionally substituted with one or more R⁷ groups, taken together with the linking nitrogen to form a 4 to 8 atom heterocyclic group)

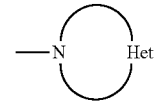

wherein;
Het represents —O—, —CH₂—, —S(O)$_r$—, —(NH)— or —(N(Alk¹-H))—;
with the proviso that
when Z is -(Alk²)$_n$-COR⁵, -(Alk²)$_n$-CO₂R⁵ or -(Alk²)$_n$-CO-thiopyridyl and R⁵ is hydrogen, -Alk¹-H, lower cycloalkyl, or adamantyl or when Z is -(Alk²)$_n$-CONR¹⁴R¹⁵ and $R^{14}$ and $R^{15}$ are
a) independently hydrogen, -Alk²-H, lower cycloalkyl, lower alkoxy, adamantyl, —Ar¹, benzyl, diphenylmethyl, triphenylmethyl or -(Alk¹)$_n$-norbornyl; or
b) carbon atoms, optionally substituted with one or more lower alkyl groups, taken together with the linking nitrogen to form a 4 to 8 atom heterocylic ring as herein before defined,
Y is hydroxy;
ii) Y is hydrogen and
Z is OR⁵, OCOR⁵, OCONR¹⁴R¹⁵, NR⁵'COR⁵, NR⁵'CO₂R⁵, NR⁵CONR¹⁴R¹⁵ or NR⁵CSNR¹⁴R¹⁵; or
iii) Y and Z taken together are =O, =CH-(Alk¹)$_n$-COR⁵, =CH-(Alk¹)$_n$-CO₂R⁵ or =CH-(Alk¹)$_n$-CONR¹⁴R¹⁵; and
$R^6$ is hydrogen or methyl;
or a pharmaceutically acceptable salt or solvate thereof.

2. A method according to claim 1 wherein the *Actinomycetes* sp. causes tuberculosis.

3. A method according to claim 2 wherein the *Actinomycetes* sp. is *M. tuberculosis, M. bovis, M. africanum, M. microti,* or a comb 4. A method according to claim 1 wherein the *Actinomycetes* sp. causes Hansen's disease.

5. A method according to claim 4 wherein the *Actinomycetes* sp. is *M. leprae*.

6. A method according to claim 1 wherein the *Actinomycetes* sp. causes pulmonary disease.

7. A method according to claim 6 wherein the *Actinomycetes* sp. is *N. asteroides* complex, *N. asteroides*, *N. farcinica*, *N. nova* or a combination thereof.

8. A method for treating a patient infected by *Actinomycetes* sp., the method comprising administering to the patient an effective amount of a 6-aza-17-substituted-androst-4-en-3-one having formula (I):

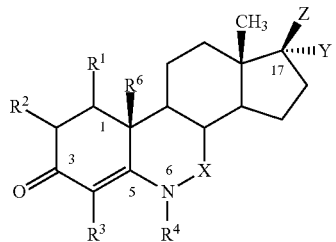

wherein:
$R^1$, $R^2$, $R^3$, $R^4$, and Y are hydrogen;
$R^6$ is methyl;
X is $CH_2$;
Z represents —$COR^5$, —$CO_2R^5$, —$COSR^5$, or —$CONR^{14}R^{15}$; wherein
  $R^5$ and $R^{5'}$ are independently hydrogen, -$Alk^1$-H (optionally substituted independently with one or more $CO_2H$, $CO_2R^7$, $Ar^2$, $Ar^3$, or cyano groups), $(Alk^1)_n$-(lower cycloalkyl (optionally substituted independently with one or more -$Alk^1$-H groups)), adamantyl, norbornyl, $Ar^2$, $Ar^3$, (lower cycloalkyl)-$Ar^2$ or (lower cycloalkyl)-$Ar^3$; wherein
    $Alk^1$ is lower alkylene, lower alkenylene or lower alkynylene;
    n is 0 or 1;
    $R^7$ is -$Alk^1$-H, -$(Alk^1)_n$-$Ar^1$ or lower cycloalkyl;
    $Ar^2$ is a homocyclic aromatic group of 6 to 14 carbon ring atoms (optionally substituted independently with one or more -$Alk^2$-H (optionally substituted independently with one or more halogens), -$(Alk^1)_n$ -$COR^7$, -$(Alk^1)_n$-OH, -$(Alk^1)_n$-$OR^{16}$, -$(Alk^1)_n$-$Ar^3$, -$(Alk^1)_n$-$CO_2H$, -$(Alk^1)_n$-$CO_2R^7$, $S(O)_rR^7$, $NR^8S(O)_rR^{16}$, $NR^8R^9$, $CONR^8R^9$, lower cycloalkyl, lower alkoxy, -$(Alk^1)_n$-$Ar^1$ (optionally substituted with one or more -$Alk^1$-H or halogen), methylenedioxy, ethylenedioxy, morpholino, thiomorpholino, cyano, nitro or halogens); wherein
    $Alk^2$ is ($C_{1-12}$) alkylene, ($C_{2-12}$) alkenylene or ($C_{2-12}$) alkynylene;
    r is 0, 1, or 2;
    $R^8$ and $R^9$ are independently hydrogen, -$Alk^1$-H or lower cycloalkyl;
    $Ar^1$ is a homocyclic aryl group of 6 to 14 carbons;
    $R^{16}$ is -$Alk^1$-H (optionally substituted independently with one or more halogens), lower cycloalkyl (optionally substituted independently with one or more halogens, or -$Alk^1$-H (optionally substituted independently with one or more halogens)) or -$(Alk^1)_n$-$Ar^1$ (wherein $Ar^1$ is optionally substituted independently with one or more lower alkoxy, cyano, halogen or -$Alk^1$-H (optionally substituted independently with one or more halogens);
    $Ar^3$ is an aromatic group of 5 to 14 ring atoms, at least one of which is O, N or S (optionally substituted independently with one or more -$Alk^1$-H (optionally substituted independently with one or more halogens), lower cycloalkyl, lower alkoxy, $CO_2H$, $CO_2R^7$, -$(Alk^1)_n$-$Ar^1$, cyano or halogen); and
  $R^{14}$ and $R^{15}$ are
    a) independently, hydroxy, hydrogen, -$Alk^2$-H, lower alkoxy, -$(Alk^1)_n$-adamantyl, -$(Alk^1)_n$-myrantyl, -$(Alk^1)_n$-norbornyl, -$(Alk^1)_n$-fluorenyl, -$(Alk^1)_n$-fluorenonyl, -$(Alk^1)_n$-indanyl (optionally substituted with one or more -$Alk^1$-H), -$Alk^1$-H (optionally substituted independently with one or more halogens, cyano, cycloalkyl, $SR^5$, $COR^5$, $CONR^5R^7$, $NR^{5'}COR^5$, $NR^{5'}CO_2R^5$, $NR^{5'}CONHR^5$, $CO_2R^5$, $OR^5$, $Ar^2$ or $Ar^3$), $Ar^2$ or $Ar^3$ or a saturated $C_{4-18}$ bicyclic ring or $C_{3-11}$ saturated ring, optionally containing an oxygen or sulfur atom (said rings optionally substituted independently with one or more cyano, $R^{16}$, $Ar^2$ or $Ar^3$); or
    b) alkylene groups (optionally substituted with one or more $R^7$ groups, taken together with the linking nitrogen to form a 4 to 8 atom heterocyclic group)

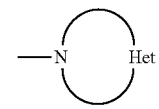

wherein;
Het represents —O—, —$CH_2$—, —$S(O)_r$—, —(NH)— or —(N($Alk^1$-H))—.

9. A method according to claim 8 wherein the *Actinomycetes* sp. causes tuberculosis.

10. A method according to claim 9 wherein the *Actinomycetes* sp. is *M. tuberculosis, M. bovis, M. africanum, M. microti*, or a combination thereof.

11. A method according to claim 8 wherein the *Actinomycetes* sp. causes Hansen's disease.

12. A method according to claim 11 wherein the *Actinomycetes* sp. is *M. leprae*.

13. A method according to claim 8 wherein the *Actinomycetes* sp. causes pulmonary disease.

14. A method according to claim 13 wherein the *Actinomycetes* sp. is *N. asteroides* complex, *N. asteroides, N. farcinica, N. nova* or a combination thereof.

15. A method for treating a patient infected by *Actinomycetes* sp., the method comprising administering to the patient an effective amount of a 6-aza-17-substituted-androst-4-en-3-one having formula (I):

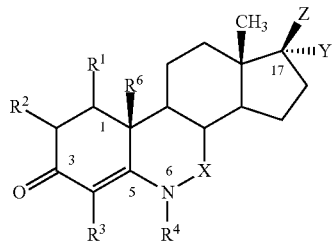 (I)

wherein:
$R^1$, $R^2$, $R^3$, $R^4$, and Y are hydrogen;
$R^6$ is methyl;
X is $CH_2$;
Z represents $—COR^5$ or $—CONR^{14}R^{15}$; wherein
  $R^5$ and $R^{5'}$ are independently hydrogen, $-Alk^1$-H (optionally substituted independently with one or more $CO_2H$, $CO_2R^7$, $Ar^2$, $Ar^3$, or cyano groups), $(Alk^1)_n$-(lower cycloalkyl (optionally substituted independently with one or more $-Alk^1$-H groups)), adamantyl, norbornyl, $Ar^2$, $Ar^3$, (lower cycloalkyl)-$Ar^2$ or (lower cycloalkyl)-$Ar^3$; wherein
  $Alk^1$ is lower alkylene, lower alkenylene or lower alkynylene;
  n is 0 or 1;
  $R^7$ is $-Alk^1$-H, $-(Alk^1)_n$-$Ar^1$ or lower cycloalkyl;
  $Ar^2$ is a homocyclic aromatic group of 6 to 14 carbon ring atoms (optionally substituted independently with one or more $-Alk^2$-H (optionally substituted independently with one or more halogens), $-(Alk^1)_n$-$COR^7$, $-(Alk^1)_n$-OH, $-(Alk^1)_n$-$OR^{16}$, $-(Alk^1)_n$-$Ar^3$, $-(Alk^1)_n$-$CO_2H$, $-(Alk^1)_n$-$CO_2R^7$, $S(O)_rR^7$, $NR^8S(O)_rR^{16}$, $NR^8R^9$, $CONR^8R^9$, lower cycloalkyl, lower alkoxy, $-(Alk^1)_n$-$Ar^1$ (optionally substituted with one or more $-Alk^1$-H or halogen), methylenedioxy, ethylenedioxy, morpholino, thiomorpholino, cyano, nitro or halogens); wherein
  $Alk^2$ is $(C_{1-12})$alkylene, $(C_{2-12})$alkenylene or $(C_{2-12})$alkynylene;
  r is 0, 1, or 2;
  $R^8$ and $R^9$ are independently hydrogen, $-Alk^1$-H or lower cycloalkyl;
  $Ar^1$ is a homocyclic aryl group of 6 to 14 carbons;
  $R^{16}$ is $-Alk^1$-H (optionally substituted independently with one or more halogens), lower cycloalkyl (optionally substituted independently with one or more halogens, or $-Alk^1$-H (optionally substituted independently with one or more halogens)) or $-(Alk^1)_n$-$Ar^1$ (wherein $Ar^1$ is optionally substituted independently with one or more lower alkoxy, cyano, halogen or $-Alk^1$-H (optionally substituted independently with one or more halogens);
  $Ar^3$ is an aromatic group of 5 to 14 ring atoms, at least one of which is O, N or S (optionally substituted independently with one or more $-Alk^1$-H (optionally substituted independently with one or more halogens), lower cycloalkyl, lower alkoxy, $CO_2H$, $CO_2R^7$, $-(Alk^1)_n$-$Ar^1$, cyano or halogen); and
  $R^{14}$ and $R^{15}$ are
    a) independently, hydroxy, hydrogen, $-Alk^2$-H, lower alkoxy, $-(Alk^1)_n$-adamantyl, $-(Alk^1)_n$-myrantyl, $-(Alk^1)_n$-norbornyl, $-(Alk^1)_n$-fluorenyl, $-(Alk^1)_n$-fluorenonyl, $-(Alk^1)_n$-indanyl (optionally substituted with one or more $-Alk^1$-H), $-Alk^1$-H (optionally substituted independently with one or more halogens, cyano, cycloalkyl, $SR^5$, $COR^5$, $CONR^5R^7$, $NR^{5'}COR^5$, $NR^{5'}CO_2R^5$, $NR^{5'}CONHR^5$, $CO_2R^5$, $OR^5$, $Ar^2$ or $Ar^3$), $Ar^2$ or $Ar^3$ or a saturated $C_{4-18}$ bicyclic ring or $C_{3-11}$ saturated ring, optionally containing an oxygen or sulfur atom (said rings optionally substituted independently with one or more cyano, $R^{16}$, $Ar^2$ or $Ar^3$); or
    b) alkylene groups (optionally substituted with one or more $R^7$ groups, taken together with the linking nitrogen to form a 4 to 8 atom heterocyclic group)

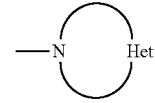

wherein;
Het represents $—O—$, $—CH_2—$, $—S(O)_r—$, $—(NH)—$ or $—(N(Alk^1\text{-}H))—$.

16. A method according to claim 15 wherein the *Actinomycetes* sp. causes tuberculosis.

17. A method according to claim 16 wherein the *Actinomycetes* sp. is *M. tuberculosis, M. bovis, M. africanum, M. microti,* or a combination thereof.

18. A method according to claim 15 wherein the *Actinomycetes* sp. causes Hansen's disease.

19. A method according to claim 18 wherein the *Actinomycetes* sp. is *M. leprae.*

20. A method according to claim 15 wherein the *Actinomycetes* sp. causes pulmonary disease.

21. A method according to claim 20 wherein the *Actinomycetes* sp. is *N. asteroides* complex, *N. asteroides, N. farcinica, N. nova* or a combination thereof.

* * * * *

UNITED STATES PATENT AND TRADEMARK OFFICE
CERTIFICATE OF CORRECTION

PATENT NO. : 8,481,530 B2
APPLICATION NO. : 12/517084
DATED : July 9, 2013
INVENTOR(S) : Sampson It is certified that error appears in the above-identified patent and that said Letters Patent is hereby corrected as shown below:

In the Specification

Column 1, lines 4-6

Now reads: "This invention was supported by a grant from NIH-NIAID, grant number R21AI065251. The United States government has rights in this invention."

Should read: --This invention was made with government support under grant number AI065261 awarded by the National Institutes of Health. The government has certain rights in the invention.--

Signed and Sealed this
Twenty-sixth Day of November, 2013

Margaret A. Focarino
*Commissioner for Patents of the United States Patent and Trademark Office*